(12) United States Patent
Sadotomo et al.

(10) Patent No.: US 7,447,294 B2
(45) Date of Patent: Nov. 4, 2008

(54) X-RAY COMPUTED TOMOGRAPHIC APPARATUS

(75) Inventors: Tetsuya Sadotomo, Otawara (JP);
Tomokazu Harada, Otawara (JP);
Makoto Nakano, Nasushiobara (JP);
Yasutaka Shindo, Nasushiobara (JP);
Katsumi Gotanda, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/470,902

(22) Filed: Sep. 7, 2006

(65) Prior Publication Data
US 2007/0053479 A1 Mar. 8, 2007

(30) Foreign Application Priority Data
Sep. 8, 2005 (JP) ............................. 2005-261009
Nov. 9, 2005 (JP) ............................. 2005-324386

(51) Int. Cl.
*H05G 1/00* (2006.01)
*H05G 1/02* (2006.01)
(52) U.S. Cl. ............................ 378/4; 378/15; 378/197
(58) Field of Classification Search .................... 378/4, 378/15, 193–197; 250/370.09
See application file for complete search history.

(56) References Cited

U.S. PATENT DOCUMENTS

| 4,217,499 A | | 8/1980 | Racz et al. |
| 5,031,198 A | * | 7/1991 | Deucher et al. ................. 378/4 |
| 5,093,850 A | * | 3/1992 | Dinwiddie et al. ............ 378/15 |
| 5,592,526 A | * | 1/1997 | Daikoku et al. ............. 378/132 |
| 5,703,921 A | | 12/1997 | Fujita et al. |
| 5,751,781 A | * | 5/1998 | Brown et al. ................... 378/65 |
| 5,761,269 A | | 6/1998 | Sugihara et al. |
| 2002/0071525 A1 | * | 6/2002 | Fenkart et al. .............. 378/203 |

FOREIGN PATENT DOCUMENTS

| GB | 1 594 274 | 7/1981 |
| JP | 8-52130 | 2/1996 |
| JP | 9-56710 | 3/1997 |
| JP | 2000-116641 | 4/2000 |

* cited by examiner

*Primary Examiner*—Irakli Kiknadze
(74) *Attorney, Agent, or Firm*—Oblon, Spivak, McClelland, Maier & Neustadt, P.C.

(57) ABSTRACT

An X-ray computed tomographic apparatus includes a cylindrical rotary base supported so as to be rotatable about a rotational axis, an X-ray tube unit mounted on the rotary base, an X-ray detecting unit mounted on the rotary base, and a reinforcing ring fixed to an end of the rotary base, and having a greater rigidity than the rotary base.

10 Claims, 7 Drawing Sheets

FIG. 11

X-RAY COMPUTED TOMOGRAPHIC APPARATUS

CROSS-REFERENCE TO RELATED APPLICATIONS

This application is based upon and claims the benefit of priority from prior Japanese Patent Applications No. 2005-261009, filed Sep. 8, 2005; and No. 2005-324386, filed Nov. 9, 2005, the entire contents of both of which are incorporated herein by reference.

BACKGROUND OF THE INVENTION

1. Field of the Invention

The present invention relates to an X-ray computed tomographic apparatus including a rotating part which rotates in order to acquire an X-ray tomographic image of a subject.

2. Description of the Related Art

An X-ray computed tomographic apparatus (hereinafter referred to as "X-ray CT (Computed Tomography) apparatus"), which provides the information on a subject as an image on the basis of the intensity of X-rays transmitted through the subject, plays an important role in many medical acts, including diagnosis of diseases, medical care, surgery planning, etc.

Such an X-ray CT apparatus has an annular rotary base. This rotary base is supported so as to be rotatable about the axial center thereof, and various devices, such as an X-ray tube, an X-ray detector, and a high-voltage generator, are fixed inside the rotary base.

Rotation of the rotary base will change the orientation of the X-ray tube and the X-ray detector. In the X-ray CT apparatus, photographing of a subject from various directions is made using a change in the orientation of the above-mentioned X-ray tube and X-ray detector (for example, refer to JP-A No. 8-52130).

Meanwhile, since the X-ray tube, the X-ray detector, the high-voltage generator, etc. have heavy weight, when the rotary base rotates at high speed, a great centrifugal force may be generated in heavy loads, such as the X-ray tube, the X-ray detector, and the high-voltage generator, which are fixed inside the rotary base, and consequently the rotary base may be deformed.

Since the angle of the X-rays radiated from the X-ray tube will deviate if the installation angle of the X-ray tube gets wrong due to deformation of the rotary base, it becomes impossible for the X-ray detector to detect the X-rays correctly. Moreover, when deviation occurs in an X-ray path, the position where X-rays are detected will change and deterioration of an image will be caused.

Hereinafter, another case will be further described as an example with reference to FIG. 11.

Figure 11:
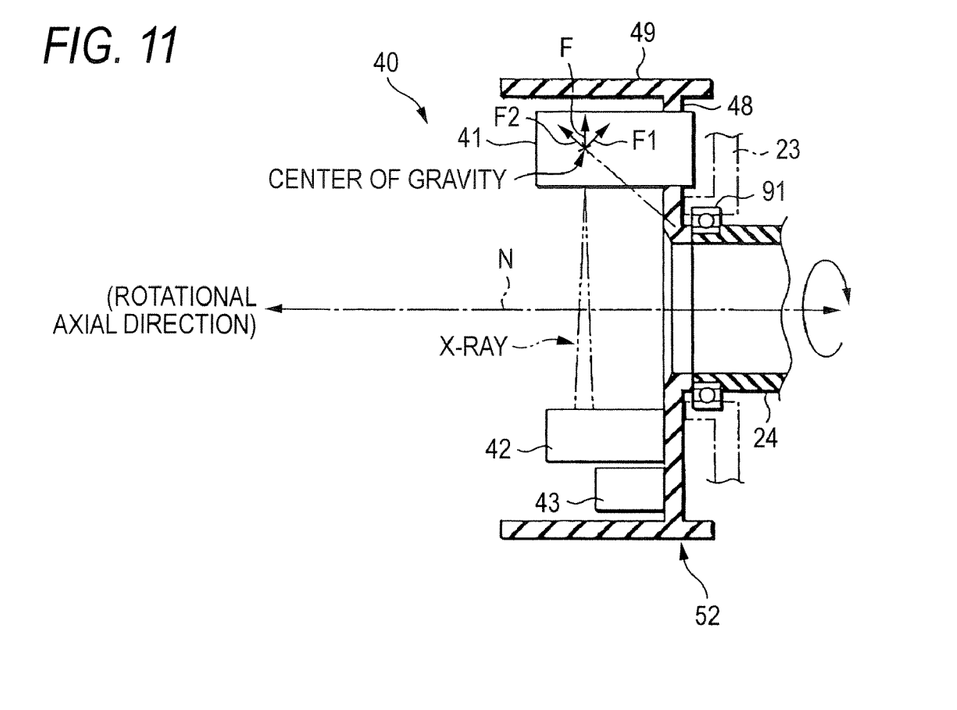
FIG. 11 is a sectional view showing the configuration of the rotating part provided within the gantry of the X-ray CT apparatus according to the second embodiment.

FIG. 11 is a sectional view showing the configuration of a conventional rotating part 40. As shown in FIG. 11, a rotating part 40 which can rotate continuously at high speed (for example, greater than 1 second/rotation) in order to acquire an X-ray tomographic image of a subject is provided in a gantry of a conventional X-ray CT apparatus. This rotating part 40 is rotatably held in a frame 23 via a bearing 91. An X-ray tube unit 41, an X-ray detecting unit 42, a signal amplification unit 43, and other units (not shown) are attached to the rotating part 40. Hereinafter, each of these units may be called a rotating part unit. Each of these rotating part units is attached to a ring-shaped flat plate part 48 (flat plate) centering on a rotational axis N.

A drum-shaped drum part 49 is formed in an outer peripheral end of the flat plate part 48. Hereinbelow, a combination of the flat plate part 48 and the drum part 49 is referred to as a rotary base 52. The rotary base 52 is held in the frame 23 via the bearing 91. The bearing 91 is sandwiched by the flat plate part 48 and the bearing holding part 24.

An X-ray CT apparatus in which each rotating part unit is attached to the inside of the drum part 49 is disclosed (see, for example, JP-A No. 2000-116641). In such a rotating part 40, the center of gravity of each rotating part unit in the direction of the rotational axis N of the rotating part 40 does not often coincide with the position of the flat plate part 48. For example, the X-ray tube unit 41 and the X-ray detecting unit 42 are disposed such that the X-rays radiated from the X-ray tube unit 41 and transmitted through a subject is detected by the X-ray detecting unit 42 disposed opposite to the X-ray tube unit 41, with the subject therebetween. That, the X-ray tube unit 41 is disposed so as to form a transmission surface of X-rays parallel to the flat plate part 48 in a position away from the flat plate part in the direction of the rotational axis N. In this case, the center of gravity of the X-ray tube unit 41 is often in the vicinity of a position where X-rays are generated. Specifically, heavy things, such as a rotor (anode) and protective lead for shielding leakage X-rays are disposed in the vicinity of the X-ray generated position. Accordingly, the center of gravity of the X-ray tube unit 41 will be in a position that is away from the flat plate part 48 in the direction of the rotational axis N. Further, since the X-ray detecting unit 42 is disposed on the side of an X-ray transmission surface of the flat plate part 48, the center of gravity of the X-ray detecting unit 42 will be in a position that is away from the flat plate part 48 in the direction of the rotational axis N, like the center of gravity of the X-ray tube unit 41. Moreover, since other rotating part units are disposed on the same side as the X-ray tube unit 41 and X-ray detecting unit 42 with respect to the flat plate part 48 from the viewpoint of easiness of work at the time of maintenance, the center of gravity often deviates, similar to the X-ray tube unit 41 or X-ray detecting unit 42.

When the rotating part 40 rotates at high speed, a centrifugal force will act on the center of gravity of each rotating part unit. For example, a centrifugal force F which acts on the X-ray tube unit 41 is shown in FIG. 11 as an example. For example, in a case where the distance from the rotational axis N to the center of gravity of the X-ray tube unit 41 is 600 mm and rotational speed is 0.5 second/rotation, the gravitational acceleration of about 10 G is generated. Further, in a case where the distance from the rotational axis N to the center of gravity of the X-ray tube unit 41 is 600 mm and the rotational speed is 0.4 seconds/rotation, the gravitational acceleration of about 15 G is generated.

Meanwhile, if the center of gravity of the X-ray tube unit 41 has deviated from the position of the flat plate part 48 in the direction of the rotational axis N as mentioned above, a component force F1 of the centrifugal force F which acts on each rotating part unit when the rotating part 40 rotates at high speed may act on a holding position of the rotary base 52 as a bending moment, and the flat plate part 48 may be deformed accordingly. Similarly, the centrifugal force may also act on the X-ray detecting unit 42 or other rotating part units to deform the flat plate part 48. Although there is a difference in deformation volume even in a case where each rotating part unit is attached to the inside of the drum part 49 as disclosed in JP-A No. 2000-116641, deformation is caused in the flat plate part 48 similarly. The deformation of the flat plate part 48 based on the centrifugal force F makes it difficult to ensure the degree of precision of the position of the X-ray transmission surface at the time of high-speed rotation.

Thus, there is also a case where the X-ray transmission surface is made wide so that the X-ray detecting unit 42 can detect X-rays with a high degree of precision. In this case, however, the amount of exposure of a subject will be increased. Further, in a case where the degree of deformation of the flat plate part 48 is great, breakage of the rotary base 52, abnormality of a CT image due to shift of CT values, etc. may be caused.

On the other hand, although there is a demand for shortening the time required for photographing a moving object, for example, a heart, etc., that is, a demand for photographing the moving object while being made to rotate at higher speed so that the object can be observed as if it stands still, the above-mentioned deformation will be increased due to the higher-speed rotation.

Further, there is also a demand for photographing an object while the rotational speed is changed. Since a centrifugal force will change if rotational speed is changed, deformation volume will also change with the change in rotational speed. Therefore, there is a fear that abnormality of a CT image may be further caused due to the change in deformation volume.

Further, although it is considered that the strength of the flat plate part 48 is raised by increasing the thickness thereof, the rotary base 52 is often fabricated of aluminum cast. In this case, if the thickness of the rotary base is increased partially, a problem occurs in flow or cooling of molten metal of the cast. As a result, there is a fear that, for example, an internal stress may be generated or the degree of precision of a shape may deteriorate. On the other hand, if the whole rotary base including the drum part 49 is thickened, the weight thereof increases, and thereby a motor to drive the rotary base is also required to be enlarged. As a result, there is a problem that the X-ray CT apparatus may be enlarged.

Further, depending on a method of reinforcing the rotary base 52, lowering of the workability at the time of maintenance as described above may be caused.

BRIEF SUMMARY OF THE INVENTION

The invention provides an X-ray computed tomographic apparatus that, even if a rotary base rotates at high speed, deterioration of image quality is hardly caused without deviation of the installation angle of an X-ray tube and a detector.

The invention provides an X-ray computed tomographic apparatus capable of reinforcing a rotary base without enlarging the apparatus.

The X-ray computed tomographic apparatus of the invention is configured as follows.

(1) An X-ray computed tomographic apparatus includes a cylindrical rotary base supported so as to be rotatable about a rotational axis, an X-ray tube mounted on the rotary base, an X-ray detector mounted on the rotary base, and a reinforcing ring fixed to the rotary base, and having a greater rigidity than the rotary base.

(2) In the X-ray computed tomographic apparatus as set forth in (1), the X-ray tube and the X-ray detector are disposed in positions offset toward the same side from a central part of the rotary base in the axial direction thereof, and the reinforcing ring is provided at an end, which is close to the X-ray tube and the X-ray detector, of the ends of the rotary base in the axial direction thereof.

(3) In the X-ray computed tomographic apparatus as set forth in claim 1, the reinforcing ring is fixed to an end face of the rotary base.

(4) In the X-ray computed tomographic apparatus as set forth in (1), the reinforcing ring is fixed to an outer peripheral face of the rotary base.

(5) In the X-ray computed tomographic apparatus as set forth in (1), the reinforcing ring is formed of any one of iron, stainless steel, and titanium.

(6) An X-ray computed tomographic apparatus includes a cylindrical rotary base supported so as to be rotatable about a rotational axis, an X-ray tube mounted on the rotary base, an X-ray detector mounted on the rotary base, and a reinforcing member fabricated of a material having a greater rigidity than the rotary base, and attached to an end of the rotary base to suppress deflection of the rotary base.

(7) In an X-ray computed tomographic apparatus having a rotating part which rotates in order to acquire an X-ray tomographic image of a subject, the rotating part includes a rotary base having a ring-shaped flat plate centering on a rotational axis of the rotating part, and a cylinder formed at an outer peripheral end of the flat plate, an X-ray tube which radiates X-rays to the subject on any one surface of the flat plate, and a reinforcing member attached to the rotary base on the other surface of the flat plate, and constituting a double structure along with the rotary base.

(8) In the X-ray computed tomographic apparatus as set forth in (7), the reinforcing member is joined to the rotary base in the vicinity of inner and outer peripheral ends of the rotary base.

(9) In the X-ray computed tomographic apparatus as set forth in (7), a hollow part is formed between the reinforcing member and the flat plate.

(10) In the X-ray computed tomographic apparatus as set forth in (7), the reinforcing member has a ring shape.

(11) In the X-ray computed tomographic apparatus as set forth in (7), the X-ray tube is attached to an inner peripheral face of the cylinder.

According to the X-ray computed tomographic apparatus, even if the rotary base rotates at high speed, deviation of the installation angle of an X-ray tube and a detector does not deviate, and deterioration of image quality is hardly caused. Moreover, it is not necessary to enlarge the apparatus.

Additional objects and advantages of the invention will be set forth in the description which follows, and in part will be obvious from the description, or may be learned by practice of the invention. The object and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First, a first embodiment of the invention will be described referring to FIGS. 1 to 5.

Figure 1:
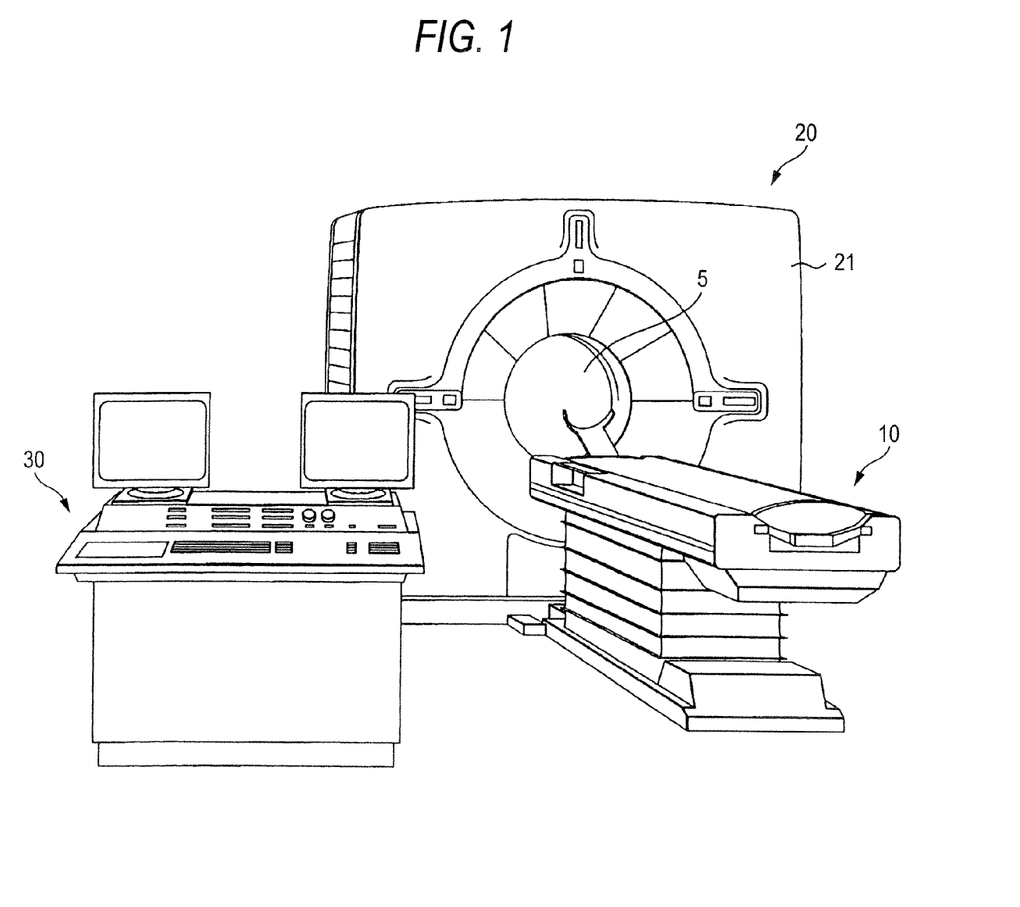
FIG. 1 is a perspective view of an X-ray CT apparatus according to the first embodiment of the invention.

FIG. 1 is a perspective view of an X-ray CT apparatus according to the first embodiment of the invention.

As shown in FIG. 1, the X-ray CT apparatus includes a gantry 20 which radiates X-rays to a subject and acquires image signals in a plurality of sections of the subject on the basis of the X-rays transmitted through the subject, a control device 30 which controls operation of the gantry 20 and creates diagnostic images in the plurality of sections of the subject on the basis of the image signals acquired by the gantry 20, and a bed 10 which positions the subject in a photographing position of the gantry 20.

An important element in this embodiment is a rotary base 11 provided within the gantry 20. Accordingly, the description of a part which is not so important in this embodiment, for example, a housing part is omitted in the following description. Further, in the description of this embodiment, the "front" indicates the near side in FIG. 1, and the "rear" indicates the rear side in FIG. 1.

Figure 2:
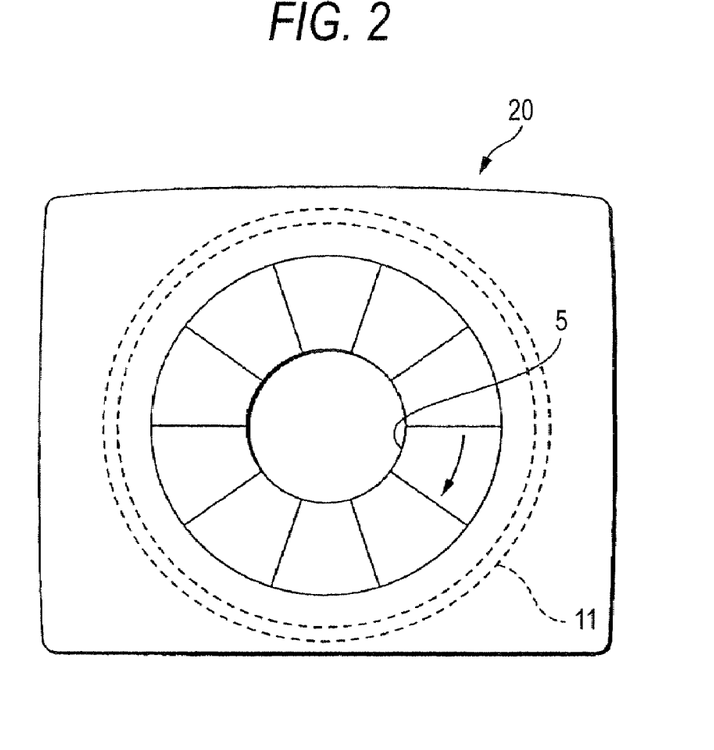
FIG. 2 is a schematic view of a gantry according to the first embodiment.

FIG. 2 is a schematic view of the gantry 20 according to this embodiment.

As shown in FIG. 2, the gantry 20 includes a photographing port 5 into which a subject is put during photographing, and a cylindrical rotary base 11 is disposed inside the gantry 20 so as to surround the photographing port 5 and to be coaxial with the photographing port 5. The rotary base 11 is rotated at high speed about the axial center of the rotary base 11 by a drive mechanism disposed within the gantry 20.

Figure 3:
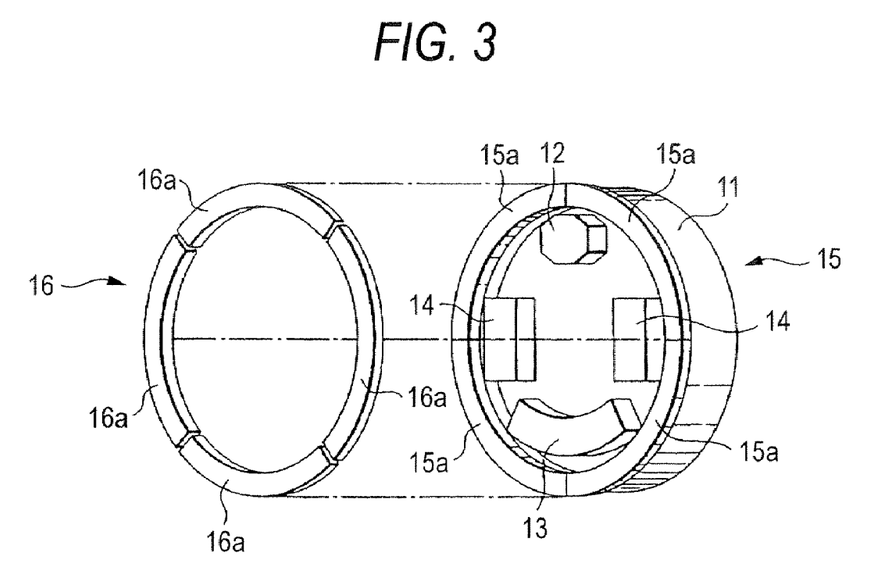
FIG. 3 is a perspective view of a rotary base according to the first embodiment.
Figure 4:
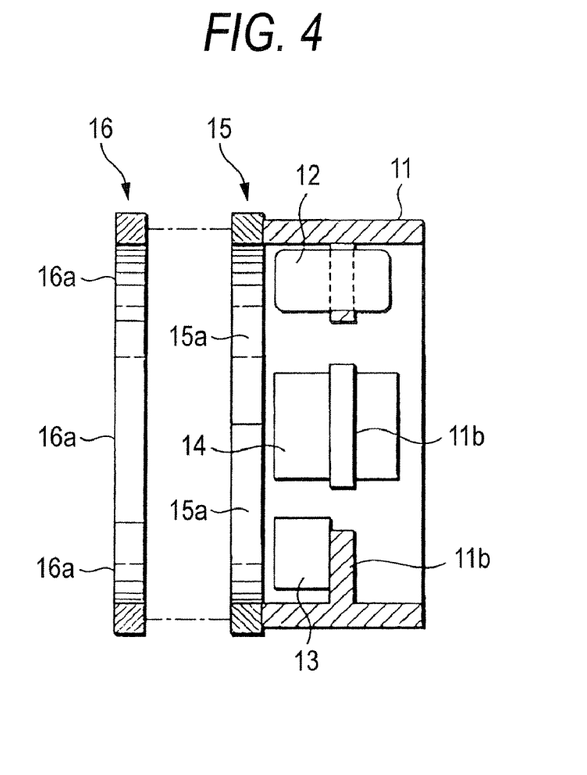
FIG. 4 is a sectional side view of the rotary base according to the first embodiment.

FIG. 3 is a perspective view of the rotary base 11 according to the first embodiment, and FIG. 4 is a sectional side view of the rotary base 11 according to the first embodiment.

As shown in FIGS. 3 and 4, the rotary base 11 has a cylindrical shape as mentioned above, and has therein fixed an X-ray tube unit 12 which radiates X-rays to a subject which is put into the photographing port 5, an X-ray detecting unit 13 which detects the X-rays transmitted through the subject, and a power unit 14 which generates a high voltage to be applied to the X-ray tube unit 12. These X-ray tube unit 12, X-ray detecting unit 13, and power unit 14 are so-called heavy loads whose weight is very heavy. Aluminum, etc. is used as a material of the rotary base 11.

The X-ray tube unit 12 is fixed to a position which is slightly offset forward from an axial central part of the rotary base 11 in an inner peripheral face of the rotary base 11. Accordingly, the center of gravity of the X-ray tube unit 12 is biased forward of the rotary base 11. Bolts are used for fixation of the rotary base 11 and the X-ray tube unit 12.

The X-ray detecting unit 13 is fixed to a front face of an attaching member 11b provided in the inner peripheral face of the rotary base 11. The attaching member 11b is disposed in substantially the central part of the rotary base 11 in the axial direction thereof. Accordingly, both the center of gravity of the X-ray detecting unit 13 fixed to the front face of the attaching member lib and the center of gravity of the X-ray tube unit 12 are biased forward of the rotary base 11. Bolts are used for fixation of the attaching member 11b and the X-ray detecting unit 13, and fixation of the attaching member 11b and the power unit 14.

A reinforcing ring 15 is fixed to a front end face of the rotary base 11 so that it may be coaxial with the rotary base 11. The reinforcing ring 15 is composed of a plurality of, for example, four circular-arc members 15a. Accordingly, the manufacture is markedly simplified compared with a case in which the reinforcing ring 15 is composed of one member. However, the reinforcing ring 15 according the invention may be a one ring-shaped member, not limited thereto.

A fixing ring 16 is disposed at a front end face of the reinforcing ring 15. The fixing ring 16 is composed of a plurality of, for example, four circular-arc fixing members 16a. Each fixing member 16a is disposed so as to cover a joint of the circular-arc members 15a constituting the reinforcing ring 15, thereby joining the adjacent fixing members 16a with bolts. Bolts (not shown) are used for fixation of the reinforcing ring 15 to the rotary base 11. The bolts may be common to the bolts which are used to join the above-mentioned reinforcing ring 15. As a material of the reinforcing ring 15, iron, stainless steel, or titanium that is a material whose rigidity is higher than aluminum is used. In addition, another fixing ring (not shown) may be disposed at the front end face of the fixing ring 16.

Next, the operation and effects of the X-ray CT apparatus having the above configuration will be described.

When the rotary base 11 rotates at high speed, a great centrifugal force will be generated in heavy loads, such as the X-ray tube unit 12, X-ray detecting unit 13, and power unit 14, which are disposed inside the rotary base, and a force which tries to spread will act on a front end of the rotary base 11.

However, the reinforcing ring 15 is fixed to the front end face of the rotary base 11 in this embodiment. Moreover, as the material of the reinforcing ring 15, iron, stainless steel, or titanium whose rigidity is higher than the material of the rotary base 11 is used.

Accordingly, even if a great force which tries to spread acts on the front end of the rotary base 1, the rotary base 11 will not be deformed by virtue of the rigidity of the reinforcing ring 15. As a result, even when the installation angle of the X-ray tube unit 12 or X-ray detecting unit 13, which are disposed inside the rotary base 11, is kept constant and the rotary base 11 rotates at high speed, a stable and clear diagnostic image is created.

Moreover, since only the reinforcing ring 15 is attached, it can be simply introduced into a conventional X-ray computed tomographic apparatus having no reinforcing ring 15. That is, even in an X-ray computed tomographic apparatus on condition of rotating the rotary base 11 at low speed, it is possible to cope with high-speed rotation of the rotary base 11 only by attaching the reinforcing ring 15.

Next, referring to FIG. 5, a reinforcing ring 17 according to a modified example of this embodiment will be described.

Figure 5:
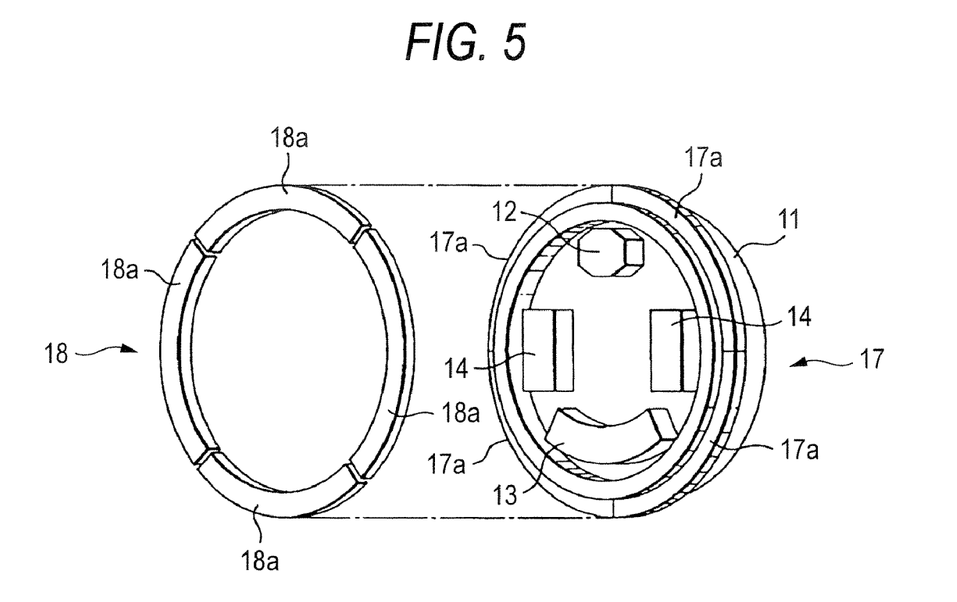
FIG. 5 is a sectional side view of a rotary base according to a modified example of the first embodiment.

FIG. 5 is a sectional side view of the rotary base 11 according to the modified example of this embodiment.

As shown in FIG. 5, the reinforcing ring 17 in this embodiment is fixed to an inner peripheral face of a front end of the rotary base 11. That is, the reinforcing ring 17 is fitted on the outside of the rotary base 11.

The reinforcing ring 17 is composed of a plurality of, for example, four circular-arc members 17a. Accordingly, the manufacture is markedly simplified compared with a case in which the reinforcing ring 17 is composed of one member. However, the reinforcing ring 17 according the invention may be a one ring-shaped member, not limited thereto.

A fixing ring 18 is disposed at a front end face of the reinforcing ring 17. The fixing ring 18 is composed of a plurality of, for example, four circular-arc fixing members 18a. Each fixing member 18a is disposed so as to cover a joint of the circular-arc members 17a constituting the reinforcing ring 17, and the adjacent reinforcing rings 18a are joined together with bolts. Bolts (not shown) are used for fixation of the reinforcing ring 17 to the rotary base 11. In addition, although this embodiment has been described about the case in which the fixing ring 18 is disposed at the front end face of the reinforcing ring 17, the fixing ring may be fixed to, for example, the outer peripheral face of the reinforcing ring 17. As a material of the reinforcing ring 17, iron, stainless steel, or titanium that is a material whose rigidity is higher than aluminum is used. In addition, another fixing ring (not shown) may be disposed at the front end face of the fixing ring 18.

In this way, when the reinforcing ring 17 is fixed to the outer peripheral face of the rotary base 11, attachment of the reinforcing ring 17 is simplified. Further, only small intensity is required for bolts used for fixation of the rotary base 11 and the reinforcing ring 17.

In addition, although this embodiment has been described about the case in which iron, stainless steel, and titanium are used as the material of the reinforcing ring 15, 17, the invention is limited thereto, and any materials may be used as long as they have rigidity higher than the material of the rotary base 11. Accordingly, the material of the reinforcing ring 15, 17 is selected according to the material of the rotary base 11.

Moreover, in this embodiment, the reinforcing ring 15, 17 is provided at the front end of the rotary base 11. However, if the centers of gravity of the X-ray tube unit 12, X-ray detecting unit 13, and power unit 14 are biased toward the rear of the rotary base 11, the reinforcing ring 15, 17 is provided at a rear end of the rotary base 11. Of course, the reinforcing rings 15, 17 may provided at front and rear ends of the rotary base 11 irrespective of the center of gravity of the X-ray tube unit 12, X-ray detecting unit 13, and power unit 14.

Furthermore, in this embodiment, bolts are used for fixation of the rotary base 11 and the X-ray tube unit 12, fixation of the rotary base 11 and the X-ray detecting unit 13, fixation of the rotary base 11 and the power unit 14, and fixation of the rotary base 11 and the reinforcing ring 15, 17. However, the invention is not limited thereto, and any means may be used as long as they can ensure firm fixation to the rotary base 11.

Second Embodiment

Next, referring to FIGS. 6 to 10, a second embodiment of the invention will be described.

Figure 6:
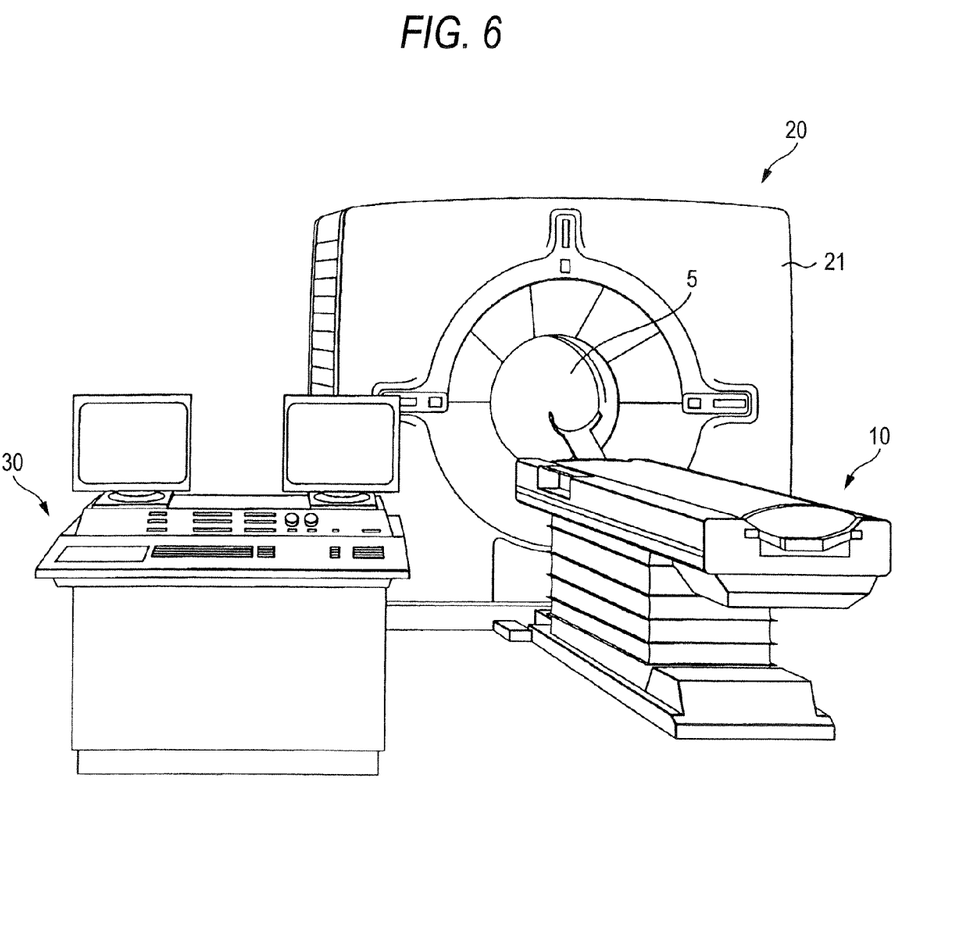
FIG. 6 is a view showing the external configuration of an X-ray CT apparatus according to a second embodiment of the invention.
Figure 7:
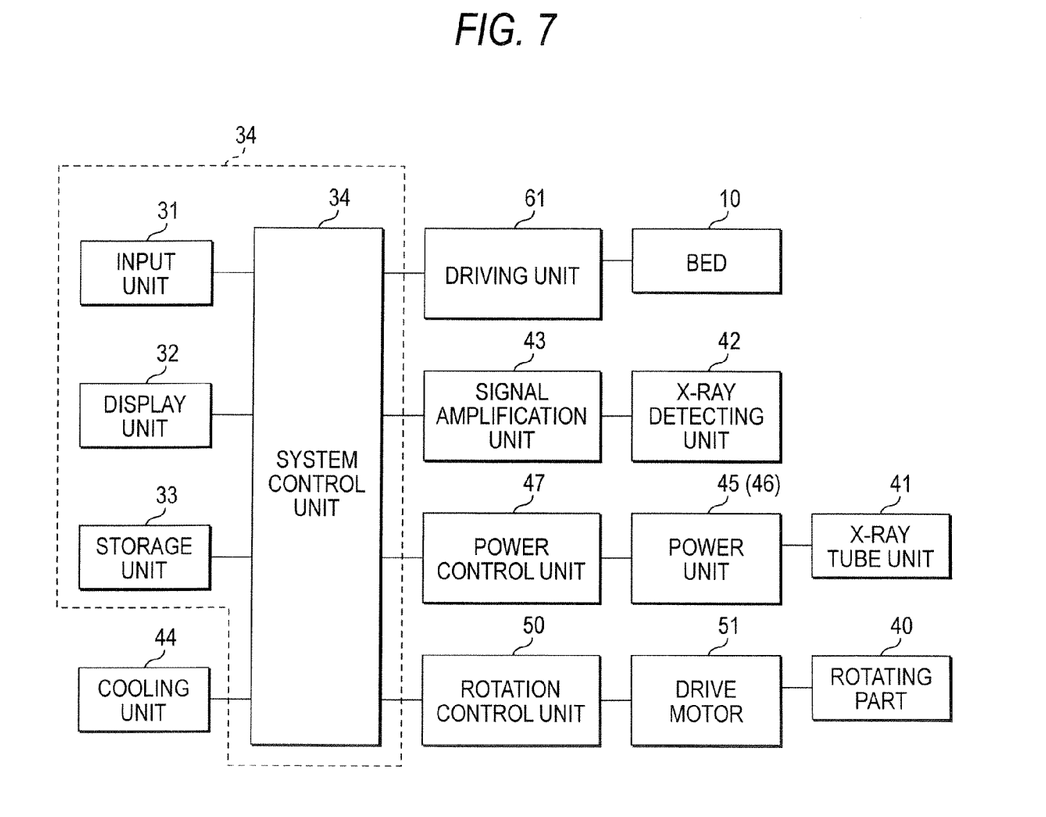
FIG. 7 is a block diagram showing the configuration of the X-ray CT apparatus according to the second embodiment.
Figure 8:
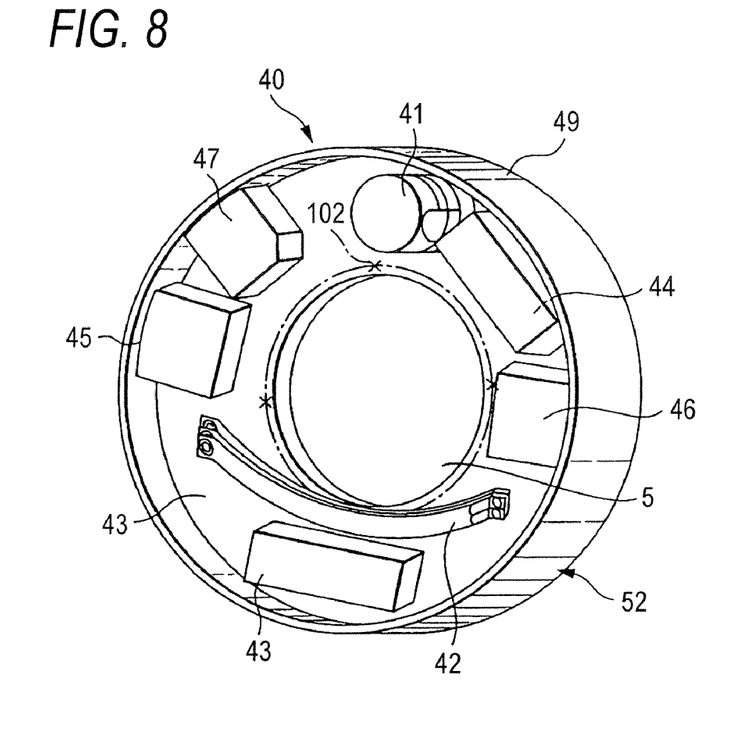
FIG. 8 is a perspective view showing the configuration of a rotating part provided within a gantry of the X-ray CT apparatus according to the second embodiment.
Figure 9:
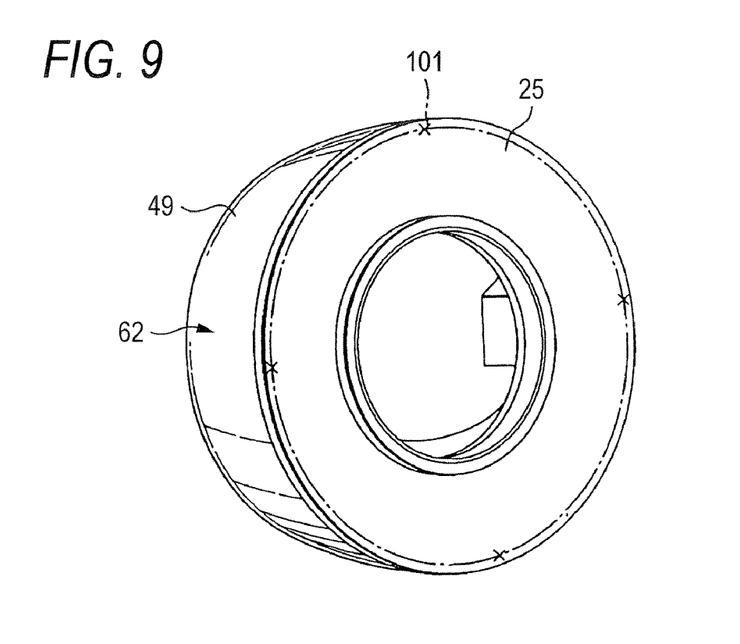
FIG. 9 is a perspective view showing the configuration of the rotating part provided within the gantry of the X-ray CT apparatus according to the second embodiment.
Figure 10:
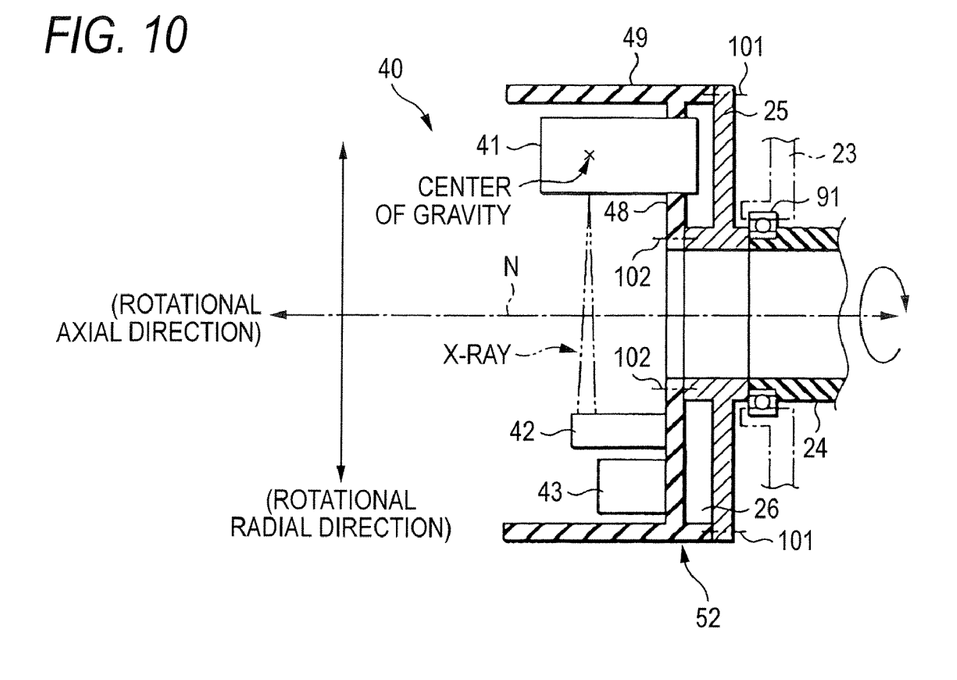
FIG. 10 is a sectional view showing the configuration of the rotating part provided within the gantry of the X-ray CT apparatus according to the second embodiment.

FIG. 6 is a view showing the external configuration of an X-ray CT apparatus of this embodiment, FIG. 7 is a block diagram showing the configuration of the X-ray CT apparatus of this embodiment, FIGS. 8 and 9 are perspective views showing the configuration of a rotating part provided in a gantry of the X-ray CT apparatus of this embodiment, and FIG. 10 is a sectional view showing the configuration of a rotating part 40 of this embodiment.

In FIG. 6, the X-ray CT apparatus of this embodiment includes a bed 10 for carrying a subject (not shown), such as a patient, a gantry 20 which has a photographing port 5 for inserting the subject and radiating X-rays, and is covered with a gantry cover 21, and a control device 30 which controls operation of the whole X-ray CT apparatus.

In a case where an X-ray CT image of a subject is acquired, the bed 10 is made to approach the gantry 20 by the driving unit 61, and the subject carried on the bed 10 is inserted into the photographing port 5 of the gantry 20. A rotating part 40 is provided within the gantry 20. As shown in FIG. 8, the rotating part includes an X-ray tube unit 41 which generates X-rays, an X-ray detecting unit 42 which is disposed opposite to the X-ray tube unit 41, with a subject therebetween, in order to detect the X-rays radiated from the X-ray tube unit 41 and transmitted through the subject, a signal amplification unit 43 which amplifies the signals detected by the X-ray detecting unit 42, a cooling unit 44 which is provided adjacent to the X-ray tube unit 41 to cool down the X-ray tube unit 41, power units 45 and 46 for supplying tube voltage (tube current) to the X-ray tube unit 41, and a power control unit 47 which controls the power units 45 and 46. The rotating part includes the X-ray tube unit 41, the X-ray detecting unit 42, the signal amplification unit 43, the cooling unit 44, the power unit 45 and 46, and the power control unit 47 (Hereinafter, each of these units each may be referred to a rotating part unit).

As shown in FIG. 7, the control device 30 includes an input unit 31 for inputting various commands required for acquisition of an X-ray CT image, a display unit 32 which displays information required for acquisition of an X-ray CT image, an acquired X-ray CT image, etc., a storage unit 33 which stores information required for acquisition of an X-ray CT image, an acquired X-ray CT image, etc., and a system control unit 34 which controls operation of each unit of the X-ray CT apparatus.

Further, the rotating part 40 is rotated by a drive motor 51 under the control of a rotation control unit 50. This rotates the rotating part 40 at high speed around a subject. In addition, the rotational speed of the rotating part 40 is, for example, more than 1 second/rotation, particularly, more than 0.5 seconds/rotation. That is, in order to obtain an X-ray CT image of a subject, the time that the rotating part 40 is required to make one rotation around a subject becomes 1 second or less, particularly, 0.5 seconds or less.

In a case where an X-ray CT image of a subject is acquired, X-rays are radiated to the subject from the X-ray tube unit 41 by supplying a predetermined tube voltage (tube current) to the X-ray tube unit 41 from the power units 45 and 46 under the control of the power control unit 47, and the X-rays transmitted through the subject are detected by the X-ray detecting unit 42 while the rotating part 40 goes around the subject. The detection signals related to the X-rays detected by the X-ray detecting unit 42 are amplified by the signal amplification unit 43, and are supplied to the system control unit 34. The system control unit 34 performs predetermined image reconstruction processing, etc. on the basis of the detection signals, to acquire an X-ray CT image, and makes the acquired X-ray CT image displayed on the display unit 32 and stored the image in the storage unit 33.

Hereinafter, the configuration of the rotating part of this embodiment will be described in detail with reference to FIGS. 8 to 10. In addition, in description of this embodiment, the bed side of the rotating part 40 will be referred to as "front side," and the opposite side will be referred to as "back side." Accordingly, the perspective view shown in FIG. 8 is referred to as a perspective view when viewed from the front side, and the perspective view shown in FIG. 9 is referred to as a perspective view when viewed from the back side. Further, the back side of the rotating part 40 is omitted in FIG. 8.

As shown in FIG. 8, the rotating part 40 is fabricated of, for example, aluminum cast, and has on the front side thereof a ring-shaped flat plate part (flat plate) 48 which rotates about a rotational axis N (refer to FIG. 10) around a subject inserted into the photographing port 5. An outer peripheral end of the flat plate part 48 is formed with a drum part (cylinder) 49 which is coaxial with the shape of a ring and wider than the width (plate thickness) of the flat plate part 48 in the direction of the rotational axis N. The drum part 49, as shown in FIG. 10, is formed from the front side of the flat plate part 48 to the rear side thereof, and a joining portion of the flat plate part 48 and the drum part 49 has a T-shaped cross section. Hereinbelow, a combination of the flat plate part 48 and the drum part 49 may be referred to as a rotary base 52.

The length of the flat plate part 48 in a rotational radial direction (refer to FIG. 10) perpendicular to the rotational axis N, i.e., the width of a ring shape is such that the X-ray detecting unit 42 is attached. Further, the X-ray tube unit 41, the X-ray detecting unit 42, the signal amplification unit 43, the cooling unit 44, the power units 45 and 46, and the power control unit 47, which are the above-mentioned rotating part units, are attached to the front side of the flat plate part 48 with fixing bolts (not shown). Further, the width of a cylinder of the drum part 49 in the direction of the rotational axis N is such that each of the above units attached to the flat plate part 48 does not protrude from the cylinder of the drum part 49 in the direction of the rotational axis N. Further, the X-ray tube unit 41 is disposed so as to form a transmission surface of X-rays parallel to the flat plate part 48 in a position away from the flat plate part 48 in the direction of the rotational axis N. Further, as discussed in "Description of Related Art," since a rotor (positive pole) and a heavy thing, such as protective lead for shielding leakage X-rays, are disposed in the vicinity of a position where X-rays are generated, the center of gravity of the X-ray tube unit 41 is often in the vicinity the X-ray generated position. That is, also in this embodiment, the center of gravity of the X-ray tube unit 41 will be in a position that is away from the flat plate part 48 toward the transmission surface of X-rays in the direction of the rotational axis N.

Further, as shown in FIGS. 9 and 10, a reinforcing member 25 is attached to the rotary base 52 on the back side of the flat plate part 48, and constitutes a double structure together with the rotary base 52. The reinforcing member 25 is fabricated of, for example, aluminum cast. In this embodiment, the reinforcing member has a ring-shaped and L-shaped section as an example like the flat plate part 48. Further, the length of the reinforcing member 25 in the rotational radial direction is almost the same as the length of the flat plate part 48 in the rotational radial direction. Further, the reinforcing member 25 is joined to the drum part 49 from the back side using fixing bolts (not shown) at a plurality of attaching parts 101 in the positions in the vicinity of an outer peripheral end of the rotary base 52. Further, the reinforcing member, as shown in FIG. 8, is joined to the flat plate part 48 from the front side using fixing bolts (not shown) at a plurality of attaching parts 102 in the positions in the vicinity of an inner peripheral end of the rotary base 52. Further, a hollow part 26 is defined between the reinforcing member 25 and the flat plate part 48. By attaching the reinforcing member 25 in this way, the geometrical moment of inertia in a direction perpendicular to the rotational axial direction increases, and consequently the strength against bending in the direction of the rotational axis N increases. Further, the hollow part 26 is formed to reduce an increase in weight, and the attaching member is simply attached along the flat plate part 48 to increase the geometrical moment of inertia and consequently further increase the strength.

Further, this embodiment illustrates an example in which the reinforcing member 25 sandwiches a bearing 91 together with a bearing holding part 24 so that the rotating part 40 is rotatably held by the frame 23 using the bearing 91.

In such a configuration, the rotary base 52 rotates about the rotational axis N, and the X-ray tube unit 41 rotates around a subject inserted into the photographing port 5. In this case, as described in "BACKGROUND OF THE INVENTION" a centrifugal force acts on the center of gravity of the X-ray tube unit 41 in a direction (outward) away from the rotational axis N, and a component force of the centrifugal force F serves as a bending moment which tends to deform the flat plate part 48 in the direction of the rotational axis N. However, since the strength of the rotary base 52 is increased by the reinforcing member 25 as described above, deformation of the rotary base 52 can be suppressed.

Accordingly, even if the rotating part 40 rotates, the degree of precision of the position of a transmission surface of X-rays can be ensured. As a result, the rotating part can be rotated at high speed, and photographing can be made while the rotational speed is changed. Further, although the rotating part unit, as shown in FIG. 8, is attached to the front side of the flat plate part 48 so that maintenance can be performed easily from the front side, the reinforcing member 25 is attached to the back side of the flat plate part 48. Thus the workability at the time of maintenance will not be lowered. Further, since the thickness of the flat plate part 48 is not increased, a problem in fabrication or deterioration of the degree of precision of a shape is not caused, for example, in a case where the rotary base 52 is fabricated of aluminum cast.

Further, although the reinforcing member 25 is formed into a ring shape in this embodiment, the reinforcing member, for example, may be formed into a shape which partially reinforces at least the vicinity of the X-ray tube unit 41, etc. as a double structure to suppress deformation.

Further, although the case in which the rotating part unit is attached to the front side of the flat plate part 48 is described as an example, the rotating part unit may be attached to the inner peripheral face (unit attaching face) of the drum part 49 like the X-ray CT apparatus described in JP-A No. 2000-116641. In this case, although a centrifugal force is received by the drum part 49, the provision of the reinforcing member 25 can suppress deformation of the rotary base 52.

Further, the attachment of the rotating part unit to the inner peripheral face of the drum part 49, similar to the X-ray CT apparatus described in JP-A No. 2000-116641, may be performed using fixing bolts, etc., or otherwise may be performed by providing a guide rail in the inner peripheral face of the drum part 49, and then causing a rotating part unit to slide along the guide rail.

The invention is not limited to the above embodiments themselves, but it can be embodied in practice by modifying constituent elements without departing the scope of the invention. Further, various inventions can be made by combinations of a plurality of suitable constituent elements disclosed in the above embodiments. For example, some constituent elements may be eliminated from all the components shown in the above embodiments.

Additional advantages and modifications will readily occur to those skilled in the art. Therefore, the invention in its broader aspects is not limited to the specific details and representative embodiments shown and described herein. Accordingly various modifications may be made without departing from the sprit or scope of the general inventive concept as defined by the appended claims and their equivalents.

What is claimed is:

1. An X-ray computed tomographic apparatus comprising:
a cylindrical ring-shaped aluminum rotary base supported so as to be rotatable about a rotational axis;
an X-ray tube mounted on the rotary base adjacent an inner surface of the rotary base;
an X-ray detector mounted on the rotary base adjacent an inner surface of the rotary base, with at least one of the barycenter of the X-ray tube and the barycenter of the X-ray detector being shifted from the center of the rotary base; and
a reinforcing ring fixed to the rotary base, and having a greater rigidity than the rotary base.

2. The X-ray computed tomographic apparatus according to claim 1,
wherein the X-ray tube and the X-ray detector are disposed in positions offset toward the same side from a central part of the rotary base in the axial direction thereof, and
the reinforcing ring is provided at an end, which is close to the X-ray tube and the X-ray detector, of the ends of the rotary base in the axial direction thereof.

3. The X-ray computed tomographic apparatus according to claim 1,
wherein the reinforcing ring is fixed to an end face of the rotary base.

4. The X-ray computed tomographic apparatus according to claim 1,
wherein the reinforcing ring is fixed to an outer peripheral face of the rotary base.

5. The X-ray computed tomographic apparatus according to claim 1,
wherein the reinforcing ring is formed of any one of iron, stainless steel, and titanium.

6. An X-ray computed tomographic apparatus comprising:
a cylindrical ring-shaped aluminum rotary base supported so as to be rotatable about a rotational axis;
an X-ray tube mounted on the rotary base adjacent an inner surface of the rotary base;
an X-ray detector mounted on the rotary base adjacent an inner surface of the rotary base, with at least one of the barycenter of the X-ray tube and the barycenter of the X-ray detector being shifted from the center of the rotary base; and
a reinforcing member fabricated of a material having a greater rigidity than the rotary base, and attached to an end of the rotary base to suppress deflection of the rotary base.

7. An X-ray computed tomographic apparatus having a rotating part which rotates in order to acquire an X-ray tomographic image of a subject, the rotating part comprising:
a rotary base including a ring-shaped flat plate centering on a rotational axis of the rotating part, and a cylinder formed at an outer peripheral end of the flat plate;
an X-ray tube which radiates X-rays to the subject on any one surface of the flat plate; and
a reinforcing member attached to the rotary base on the other surface of the flat plate, and constituting a double structure along with the rotary base,
wherein a hollow part is formed between the reinforcing member and the flat plate.

8. The X-ray computed tomographic apparatus according to claim 7,
wherein the reinforcing member is joined to the rotary base in the vicinity of inner and outer peripheral ends of the rotary base.

9. The X-ray computed tomographic apparatus according to claim 7, wherein the reinforcing member has a ring shape.

10. The X-ray computed tomographic apparatus according to claim 7,
wherein the X-ray tube is attached to an inner peripheral face of the cylinder.

* * * * *